United States Patent [19]

Shimamura

[11] Patent Number: 5,358,713
[45] Date of Patent: Oct. 25, 1994

[54] **METHOD OF PREVENTING THE TRANSMISSION OF INFECTION CAUSED BY METHICILLIN-RESISTANT *STAPHYLOCOCCUS AUREUS***

[75] Inventor: Tadakatsu Shimamura, 4-4, Nishihara 1-chome, Shibuya-ku, Tokyo, Japan

[73] Assignees: Mitsui Norin Co., Ltd.; Tadakatsu Shimamura, both of Tokyo, Japan

[21] Appl. No.: 96,060

[22] Filed: Jul. 22, 1993

Related U.S. Application Data

[63] Continuation of Ser. No. 831,003, Feb. 6, 1992, abandoned, which is a continuation of Ser. No. 580,808, Sep. 11, 1990, abandoned.

[30] Foreign Application Priority Data

Feb. 23, 1990 [JP] Japan .................................. 2-42984

[51] Int. Cl.$^5$ ...................... A61K 35/78; C12N 11/02; C07C 69/88
[52] U.S. Cl. ................................ 424/195.1; 435/177; 560/68
[58] Field of Search ..................... 424/195.1; 435/177; 560/68

[56] References Cited

U.S. PATENT DOCUMENTS

| | | | |
|---|---|---|---|
| 333,632 | 1/1886 | Homero | 424/195.1 |
| 4,585,738 | 4/1986 | Roland | 435/176 |
| 4,613,672 | 9/1986 | Hara | 549/399 |
| 4,673,530 | 6/1987 | Hara | 252/398 |
| 4,840,966 | 6/1989 | Hara | 514/456 |
| 4,913,909 | 4/1990 | Hara et al. | |

FOREIGN PATENT DOCUMENTS 0397914 11/1990 European Pat. Off.
61-130285 6/1986 Japan.

OTHER PUBLICATIONS

Hagers Handbuch der Pharmazeutischen Praxic, 1972 4th Ed. vol. 3, Editors List & Horhammer pp. 626–646.
The Merck Index 9th Ed. Merck & Co. Rahway N.J. 1976 #1898, #8987.
Chemical Abstracts 107 #19 Nov. 9, 1987 p. 388 #107:172303v.
Mori et al., "Antibacterial Activity and Mode of Action of Plant Flavonoids Against Proteus Vulgaris and *Staphylococcus Aureus*", Phytochemistry, 26, 2231–2234, (1987).
Biological Abstracts, vol. 73, No. 1, 1982, p. 248, abstract no. 2351.
Biological Abstracts, vol. 76, No. 4, 1983, p. 2633, abstract No. 24362.
Biological Abstracts, vol. 88, No. 2, 1989, p. AB-328, Abstract No. 129649.
Chemical Abstracts, vol. 113, No. 3, Jul. 16, 1990, p. 525, Abstract No. 22430u.

*Primary Examiner*—Michael G. Wityshyn
*Assistant Examiner*—Ralph Gitomer
*Attorney, Agent, or Firm*—Frishauf, Holtz, Goodman & Woodward

[57] ABSTRACT

A method for preventing infection caused by an antibiotic-resistant staphylococcus, which includes applying an effective antibacterial amount of tea or a tea polyphenol to an individual.

14 Claims, 1 Drawing Sheet

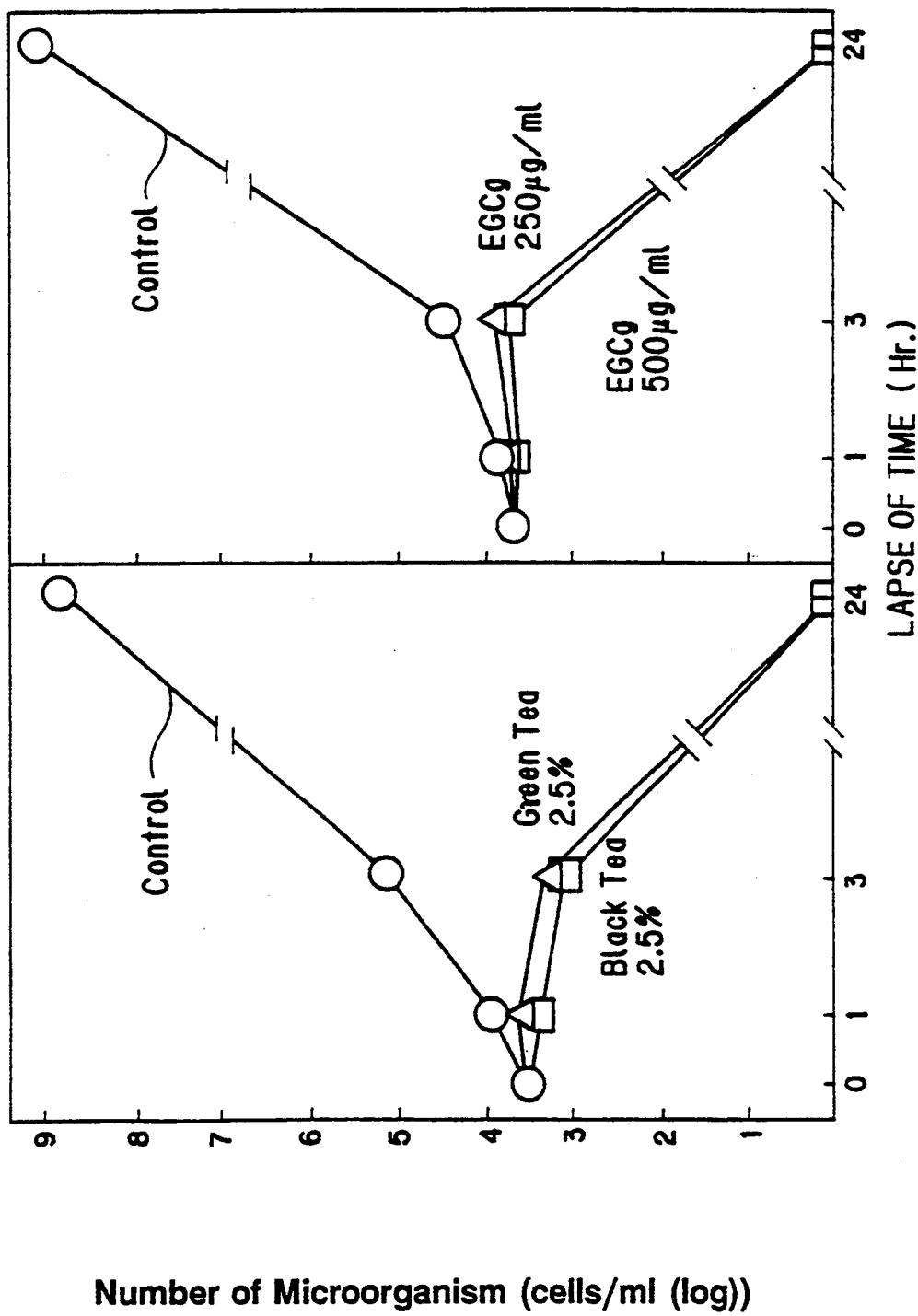

METHOD OF PREVENTING THE TRANSMISSION OF INFECTION CAUSED BY METHICILLIN-RESISTANT STAPHYLOCOCCUS AUREUS

This application is a continuation, of application Ser. No. 07/831,003, filed Feb. 6 1992, now abandoned, which is a continuation of application Ser. No. 07/580,808 filed Sep. 11, 1990 (abandoned).

BACKGROUND OF THE INVENTION

1. Field of the Invention

The present invention relates to an agent for preventing the infection with an antibiotic-resistant staphylococcus. More particularly, the present invention relates to an agent for preventing the infection with an antibiotic-resistant staphyloccocus, which has a bactericidal action to a methicillin-resistant Staphylococcus aureus.

2. Background Information

A staphylococcus, that is, Staphylococcus aureus, is a most popular bacterium causing a bacterium-infectious disease, and is normally present in the affected part of purulent inflammation, an environment and the skin, nose and pharynx of a man. Since this bacterium produces exotoxins represented by an enterotoxin and exoenzymes, the bacterium has highly pathogenic properties and causes various diseases such as infectious diseases of the skin and flesh, infectious diseases of intestinal tracts (food poisoning), septicemia, endocarditis, cerebromeningitis, infectious diseases of the respiratory organs and infectious diseases of urinary passages. Furthermore, it is known that the bacterium causes staphylococcal (scald) skin diseases and so-called toxic shock diseases, that is, serious systemic diseases entailing various clinical symptoms such as sudden fever, eruption and hypotension. Since the staphylococcus is a bacterium, antibiotics are administered for prevention and remedy of these infectious diseases. However, the presence of a so-called antibiotic-resistant staphylococcus, to which no effect is manifested by administration of antibiotics, becomes known, and the remedy or prevention is greatly hindered.

Therefore, development of a medical agent capable of effectively preventing infectious diseases caused by an antibiotic-resistant staphylococcus, which has no harmful adverse action to a human body and can be administered with safety, is eagerly desired.

SUMMARY OF THE INVENTION

Under this background, inventor searched for a substance capable of preventing the infection with an antibiotic-resistant staphylococcus by killing the staphylococcus among natural substances other than chemical synthetic substances, and inventor found that a substance having such a function is present in tea and tea polyphenols. I have now completed the present invention based on this finding.

More specifically, in accordance with the present invention, there is provided an agent for preventing the infection with an antibiotic-resistant staphylococcus, which comprises tea as an effective component.

BRIEF DESCRIPTION OF THE DRAWING

FIG. 1 is a graph illustrating the relation between the culture time and the number of cells.

DETAILED DESCRIPTION OF THE INVENTION

A principal component of tea is tea polyphenol compounds, an said tea polyphenol compounds include the tea catechin compounds represented by the general formula (I) given below and the theaflavin compounds represented by the general formula (II) given below, and also thearubigin:

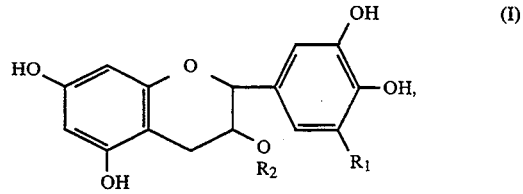

in which $R_1$ is a hydrogen atom or a hydroxy group and $R_2$ is a hydrogen atom or a 3,4,5-trihydroxy benzoyl group; and

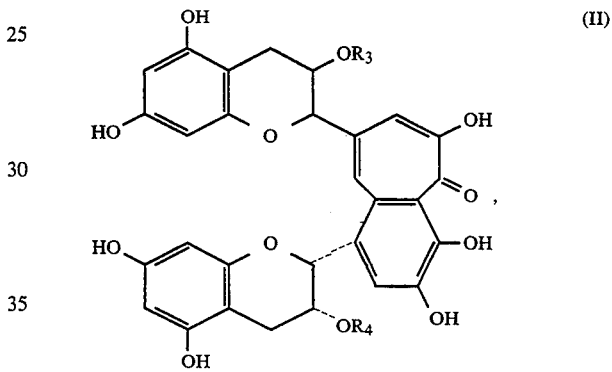

in which $R_3$ and $R_4$ are, each independently from the other, a hydrogen atom or a 3,4,5-trihydroxy benzoyl group.

Particular examples of the tea catechin compounds represented by the general formula (I) include: (+)-catechin, (−) epicatechin, which is a compound of the formula (I) with $R_1=H$ and $R_2=H$; (−) epigallocatechin, which is a compound of the formula (I) with $R_1=OH$ and $R_2=H$; (−)epicatechin gallate, which is a compound of the formula (I) with $R_1=H$ and $R_2=3,4,5$-trihydroxy benzoyl group; and (−)epigallocatechin gallate, which is a compound of the formula (I) with $R_1=OH$ and $R_2=3,4,5$-trihydroxy benzoyl group. Particular examples of the theaflavin compounds include: free theaflavin, which is a compound of the formula (II) with $R_3=H$ and $R_4=H$; theaflavin monogallate A, which is a compound of the formula (II) with $R_3=3,4,5$-trihydroxy benzoyl group and $R_4=H$; theaflavin monogallate B, which is a compound of the formula (II) with $R_3=H$ and $R_4=3,4,5$-trihydroxy benzoyl group; and theaflavin digallate, which is a compound of the formula (II) with $R_3=3,4,5$-trihydroxy benzoyl group and $R_4=3,4,5$-trihydroxy benzoyl group.

The above described tea polyphenol compounds can be prepared from tea leaves as the starting material and a method for the preparation thereof and a typical example of the product composition are described, for example, in Japanese Patent Kokai 59-219384, 60-13780 and 61-130285, etc.

An objective antibiotic-resistant staphylococcus is a methicillin-resistant Staphylococcus Aureus (MRSA) including a staphylococcus having a resistance to other antibiotics.

When the agent for preventing the infection with the antibiotic-resistant staphylococcus according to the present invention is used as a medical agent or is added to a food and the like, the above-mentioned tea polyphenol as the main component or tea is directly dissolved in water or an alcohol and the solution is used. Of course, an aqueous solution can be drunk or can be used as a hand-washing antiseptic solution. The concentration of tea at the time of application is preferably 1/10 to 1 of the ordinary drinking concentration (2 g/100 ml), and the concentration of the tea polyphenol is preferably 50 to 2000 ppm. It is especially preferred that the concentration of tea be ⅓ to 1 of the ordinary drinking concentration and the concentration of the tea polyphenol be 50 to 1000 ppm.

Since the agent for preventing the infection with an antibiotic-resistant staphylococcus according to the present invention comprises a substance daily drunk in a considerable quantity as the main component, there is no fear of an adverse side effect on a human body and shows a strong antibacterial activity to the antibiotic-resistance staphylococcus. Therefore, the agent for preventing the infection with an antibiotic-resistant staphylococcus according to the present invention is very effective for preventing the infection with an antibiotic-resistant staphylococcus.

The present invention will now be described in detail with reference to the following examples that by no means limit the scope of the invention.

EXAMPLE 1

(1) Preparation of Tea Extract, Tea Polyphenols and Solution of Antibiotic

Black tea and green tea extracts were prepared by carrying out extraction with a phosphate buffer saline (PBS) so that the concentration was 20 w/v %. Furthermore, (−)-epigallocatechin gallate (EGCg), theaflavin digallate (TF3) and minomycin (MINO) as a control antibiotic were independently dissolved in PBS at concentrations of 1.25 mg/ml, 2.5 mg/ml and 5 µg/ml, respectively.

(2) Strains

As MRSA, there were used 30 strains separated at the Showa University Hospital, 22 strains separated at the Fujigaoka Hospital of Showa University and one other strain, 53 strains as a whole. As the standard strain, there were used Staphylococcus aureus ATCC 25923, Staphylococcus aureus ATCC 12598, Staphylococcus aureus ATCC 209, and three other strains, 6 strains as a whole. Furthermore, 20 strains of Staphylococcus aureus separated from food poisoning materials were used at the experiments.

(3) Measurement of Antibacterial Activity

The measurement of the antibacterial activities of black tea and green tea extracts, EGCg, TF3, and MINO as the control was carried out according to the customary agar well (sample: 50 µl) method using Mueller-Hinton medium (10 ml). Moreover, the test was conducted to antibiotic substances, ampicillin (PcA, 2 µg, 5 µg, 20 µg) and oxacillin (PcM, 0.5 µg, 2 µg, 10 µg) according to the three-concentration disk method.

As the result, it was found that among 53 strains of MRSA, 25 strains were resistant to MINO. All of 53 strains were resistant to PcM, and 28 strains were resistant to PcA and 25 strains were slightly resistant to PcA. In contrast, all of the strains were sensitive to black tea, green tea, EGCg and TF3, and it was found that black tea, green tea, EGCg and TF3 had an effective antibacterial activity. The standard strains and the strains of Staphylococcus aureus derived from the food poisoning materials were sensitive to MINO, PcA and PcM and also sensitive to green tea, black tea, EGCg and TF3.

EXAMPLE 2

It was checked whether or not the propagation in a culture medium of MRSA could be inhibited. Culture media were prepared by adding black tea (2.5%), green tea (2.5%) or EGCg (250 or 500 µg/ml) to ordinary bouillon, and an additive-free control bouillon medium was similarly prepared. Each medium was inoculated with an equal number of cells of the Hatanodai strain (separated from a patient) of MRSA, and culturing was carried out according to customary procedures.

The relation between the culture time and the number of cells is shown in FIG. 1. It is seen from FIG. 1 that in the control medium, the number of cells logarithmically increased, and that when green tea, black tea or EGCg was added, the number of cells gradually decreased and cells were completely annihilated after 24 hours.

What is claimed is:

1. A method of preventing the transmission of an infection caused by methicillin-resistant Staphylococcus aureus comprising applying to a human host to be protected or a human host who has been infected, an effective antibacterial amount of a tea polyphenol.

2. The method as claimed in claim 1, wherein the tea polyphenol is at least one catechin.

3. The method as claimed in claim 2, wherein the at least one catechin is selected from the group consisting of epigallocatechin gallate, epicatechin gallate, epicatechin and (+)-catechin.

4. The method as claimed in claim 1, wherein the tea polyphenol is at least one tea polyphenol selected from the group consisting of epigallocatechin gallate, epicatechin gallate, epigallocatechin, epicatechin, catechin, free theaflavin, theaflavin monogallate A, theaflavin monogallate B and theaflavin digallate.

5. The method as claimed in claim 4, wherein the tea polyphenol is in an alcoholic solution.

6. The method as claimed in claim 4, wherein the tea polyphenol is in an aqueous solution at a concentration of 50 to 2000 ppm.

7. The method as claimed in claim 4, wherein the tea polyphenol is in an aqueous solution at a concentration of 50 to 1000 ppm.

8. The method as claimed in claim 4, wherein the tea polyphenol is orally administered.

9. The method as claimed in claim 4 wherein the tea polyphenol is applied topically in the form of a hand-washing solution.

10. The method as claimed in claim 4, wherein the tea polyphenol is an isomer of a catechin compound selected from the group consisting of epigallocatechin gallate, epicatechin gallate, epigallocatechin, epicatechin and catechin.

11. The method as claimed in claim 4, wherein the tea polyphenol is (−)-epigallocatechin gallate.

12. The method as claimed in claim 4, wherein the tea polyphenol is selected from the group consisting of free theaflavin, theaflavin monogallate A, theaflavin monogallate B and theaflavin digallate.

13. The method as claimed in claim 4, wherein the tea polyphenol is selected from the group consisting of (−)-epicatechin, (−)-epigallocatechin, (−)-epicatechin gallate and (−)-epigallocatechin gallate.

14. The method as claimed in claim 4, wherein the tea polyphenol is (+)-catechin.

* * * * *